United States Patent [19]
Anascavage et al.

[11] Patent Number: 5,887,707
[45] Date of Patent: Mar. 30, 1999

[54] DENTAL PROSTHESIS COMPONENT DISPLAY

[76] Inventors: Gregory T. Anascavage, 2 Atlanta, Irvine, Calif. 92620; Howard Blonder, 10933 Lakewood Blvd., Downey, Calif. 90241

[21] Appl. No.: 932,161
[22] Filed: Sep. 17, 1997
[51] Int. Cl.[6] .................................................. B65D 25/00
[52] U.S. Cl. .......................... 206/63.5; 206/771; 220/334
[58] Field of Search .................................. 206/438, 63.5, 206/6.1, 566, 467, 468, 469, 470, 775, 776, 778, 781, 782, 769, 771; 220/334, 339

[56] References Cited
U.S. PATENT DOCUMENTS 4,396,121  8/1983  Lemmon ................................ 206/566
5,407,066  4/1995  Grange ................................ 206/467 X Primary Examiner—Jacob K. Ackun

[57] ABSTRACT

A dental prosthesis component container and display system for containing sterile dental prostheses and components thereof for convenient use by a dentist or oral surgeon comprising a resiliently flexible envelope in a component box, the dental prosthesis component being inside the resiliently flexible envelope, the resiliently flexible envelope being under bending stress such that when the top of the component box is opened such stress is relieved by extension of the envelope through the open top is disclosed.

21 Claims, 3 Drawing Sheets

DENTAL PROSTHESIS COMPONENT DISPLAY

FIELD OF THE INVENTION

This invention relates to dental prosthesis technology.

BACKGROUND OF THE INVENTION

Dental prosthesis technology is very well developed and there is a large body of literature describing this technology in technical reports, professional literature and patents. Indeed, within the past decade, this has become a very crowded art.

The prior art discloses a vast array of dental prosthesis components. For convenience, the term "prosthetic components" or simply "prosthesis" will be used herein as a shorthand reference to all of the components of a dental restoration or other procedure that involves the implantation of a dental implant, pin, screw or other device into the jaw of a patient, including the components attached thereto, such as abutments, copings, prostheses per se, and attaching components, such as screws, pins, and washers, etc. The reader is referred to the following United States Patents to illustrate, in general, a few of the types of components that may be used: U.S. Pat. No. 5,476,382 to Daftary; U.S. Pat. No. 5,431,576 to Daftary; U.S. Pat. No. 5,431,567 to Daftary; U.S. Pat. No. 5,030,096 to Hurson, et. al; and U.S. Pat. No. 4,856,648 to Krueger.

The components used in dental prosthesis technology are very small; they are so small, indeed, that in many instances it is impossible visually to distinguish between different sizes, and sometime even between different components. Magnification and/or the use of calipers or other measuring devices is often necessary to ascertain exactly the type and size of the component.

A great variety of types and sizes of components must be kept on hand to assure that the dentist or oral surgeon has the right type of component in the right size to treat a patient. Sometimes, a preliminary procedure or examination enables the doctor to determine in advance the type and size of dental prostheses, abutment, coping, etc., that will be required. However, a change of type or size may be required while a procedure is being carried out as a result of the discovery of a problem not previously known, or some other circumstance which cannot be fully determined until the procedure begins. Often,. of course, the type or size of a dental prosthesis component is unknown or cannot be determined until a dental or surgical procedure is begun. In all cases, however, it is important that the doctor have on hand a substantial number of components to assure that the proper components are on hand.

Dental prosthesis components, being very small, are difficult to handle. Many are so small that extremely well developed manual dexterity is required simply to hold them in a given position and special holding tools are required to use them.

Efforts have been made to provide packaging and holders to enable the doctor to identify, select and/or to hold the component and to use the component in a dental or surgical procedure. U.S. Pat. No. 4,856,648 to Krueger, U.S. Pat. No. 5,290,171 to Daftary and U.S. Pat. No. 5,030,096 to Hurson, et. al., are exemplary of such efforts.

A companion problem is that of maintaining sterility of the dental prosthesis component. Such components are frequently pre-sterilized by the manufacturer in a sealed package or envelope. Sterility is reliably obtained and reasonably assured so long as the sterile package is not opened or damaged. The dentist often finds it difficult to handle these small components and yet maintain sterility. The component must be removed from the sterile package and transferred to the opening in the patient=s mandible or maxilla directly or by way of a sterile surgical holder or instrument. Removing the small component from the package while maintaining sterility is a serious inconvenience. Facets of this problem, and examples of the types of components of concern, are addressed in the following U.S. Pat. Nos.: 4,976,617 to Carchidi; 4,941,227 to Sussman; 5,062,800 to Niznick; 5,290,171 to Daftary, et. al.,; 5,368,160 to Leuschen, et. al.; 5,538,428 to Staubli; 5,558,230 to Fischer, et. al.; and 5,582,299 to Lazzara et. al. One facet of the present invention addresses this problem.

Many efforts have been made in this crowded art to provide the doctor with dental implants and dental prostheses and components thereof in a way that will permit quick and certain size and component identification and provide means for handling dental prosthesis components, there remains the need for a compact orderly system and apparatus to minimized space requirements in the doctor=s operating room and, at the same time, present the components in a convenient manner for identification, handling and use. This invention meets this need more efficiently and more conveniently that any system or apparatus of which the inventors are aware.

SUMMARY OF THE INVENTION

The present invention is embodied in a dental prosthesis component container and display system for containing sterile dental implants and prostheses and components thereof for convenient use by a dentist or oral surgeon. The system comprises, in combination, a display package comprising a base and a transparent cover. The base, which is preferably sterilizable, comprises a peripheral frame defining a shallow receptacle compartment. The cover, which may be sterilizable, is formed entirely or in substantial part of transparent material and is constructed and configured to fit snugly over and extend above the base. The combined base and cover define an enclosure which is visible through the cover from outside the enclosure. A plurality of component boxes constructed and configured to fit inside the enclosure in at least one symmetrical column front to back are so disposed inside the enclosure. Each of the boxes comprises a bottom, walls and an openable top to define a component containing space. A component of a dental implant or dental prosthesis is contained inside the component box.

Indicia on the component boxes encode information defining the size of the dental implant or dental prosthesis or component thereof contained in the box.

Indicia on the component boxes depict the dental implant or dental prosthesis or component in the box.

In a preferred embodiment, a resiliently flexible envelope is in each of the component boxes, the dental implant or dental prosthesis or a component of a dental implant or dental prosthesis is inside the resiliently flexible envelope. The resiliently flexible envelope is so configured and constructed that when it is contained in the component box it is under bending stress and when the top of the component box is opened such stress is relieved by extension of the envelope through the open top.

In a preferred embodiment, the individual component boxes comprise a bottom, front wall, back wall and an openable top define a component containing space. The back wall comprises an upper back wall portion, a step portion extending toward the front wall and a lower back wall portion and is so configured and constructed that the bottom and lower back wall of each component box fits into an individual box receiving receptacle with the step extending over the divider and the upper back wall portion extending upwardly over the divider, thus disposing the boxes in a front-to-back symmetrical columnar configuration.

DESCRIPTION OF THE PREFERRED EMBODIMENTS

Figure 1:
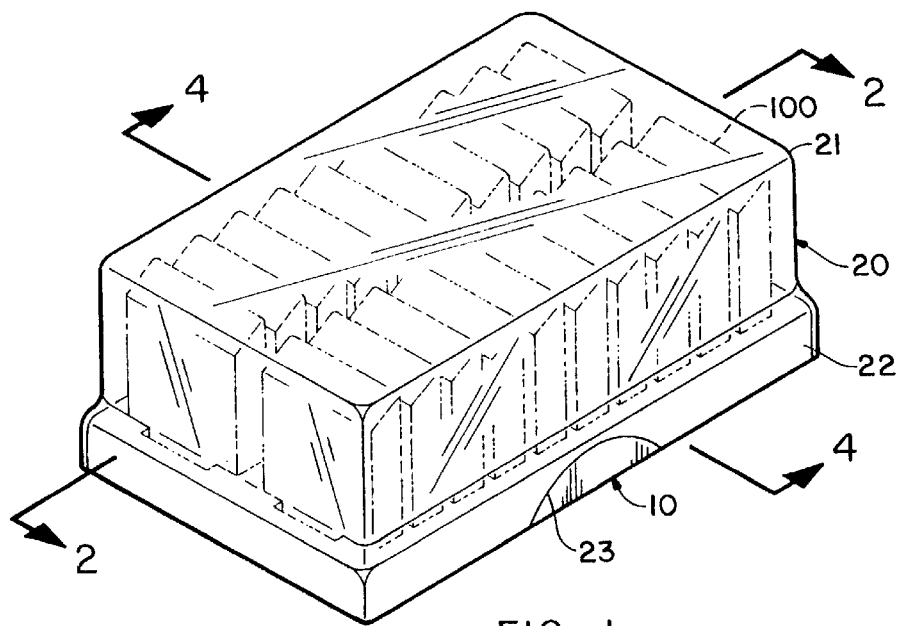
FIG. 1 is a perspective view of one of several dental prosthesis component display packages which, in combination, make up the orderly system of packaging and holding such components of this invention. A plurality of such packages can be nested one on top of the other, permitting the package of current interest to reside on top to display components of a predetermined size and/or type.

The following description and the exemplary embodiments depicted in the drawings disclose the best form of the invention presently known to the inventors. Neither the description nor the drawings are, however, limiting. There are many facets to the invention. The invention can be made of a combination of any of a large number of materials. The configuration of each of the individual components may vary considerably, so long as the relationship permits display and use. Indeed, many variations and adaptations can be made within the spirit of the invention and without departing from the claims. Thus, the specification and drawings are exemplary, not limiting.

Figure 2:
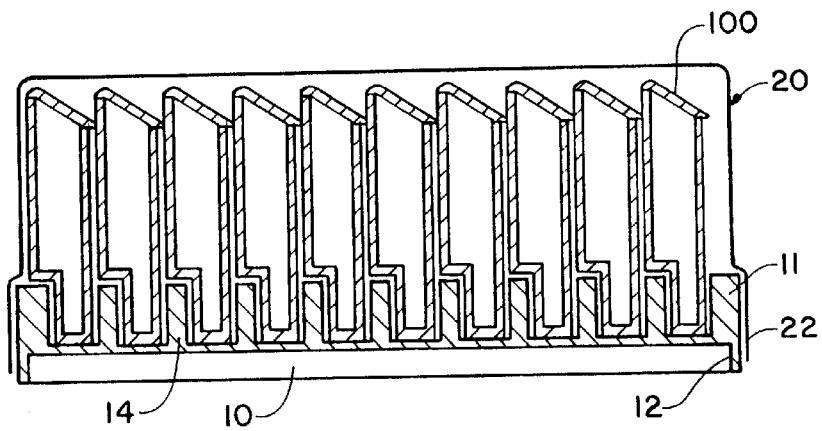
FIG. 2 is a cross-sectional view of the package of FIG. 1 taken along lines 2—2 as shown in FIG. 1.
Figure 3:
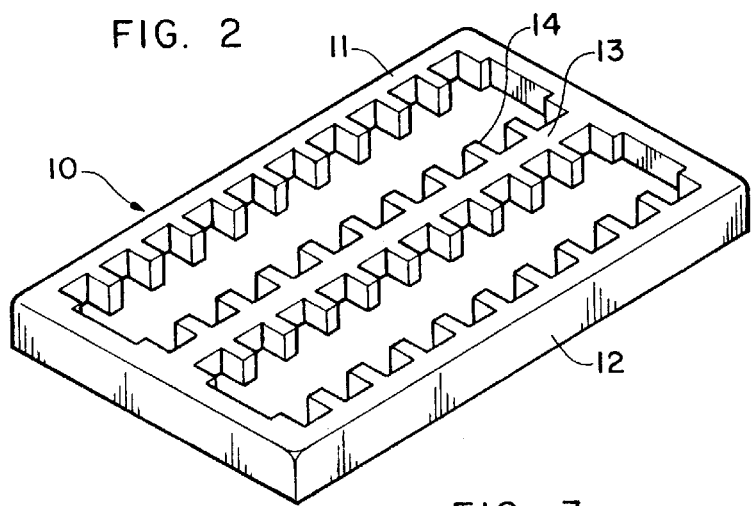
FIG. 3 is a top perspective view of the base of the package shown in FIG. 1.

The display package, depicted in perspective in FIG. 1 and depicted in other views in FIGS. 2 through 5, comprises a base 10 and a cover 20. The base is in the form of a specially designed tray having a rectangular peripheral frame 11, which includes a downwardly extending lip 12, surrounding a shallow receptacle compartment separated, in the preferred embodiment, by a central bar 13 into two receptacle compartments. Each of the compartments is wholly or partially separated into a plurality of subcompartments by a pair of spacers 14 or, if preferred, by a pair of such spacers joined to form a single structure. The lip 12 extends downwardly from the periphery of the base to enable and define a nesting relationship The preferred form of the base is depicted in FIG. 3, however, many variations as to detail are possible. The base may, for example, may comprise a single receptacle compartment, or three or more such compartments. Dimensions are not critical, but the tray, and the display package must be small enough to be light and easily handled in the operating room. A base which is six inches by eight to ten inches is convenient. The base is made of a sterilizable material.

The cover 20 is configured, constructed and dimensioned to fit over the base and to receive a base on the top thereof, the lip 12 of the base extending around the upper periphery of the cover to secure the base in position thereon. The base, thus, comprises a generally rectangular enclosure 21 with downwardly extending lip 22 which are configured and dimensioned to slip down over the periphery of the base. There is, of course, a transitional section between the upper part of the cover, which is constructed and configured to receive the lip 12 of the base, and the lower lip portion 22 which is constructed and configured to fit down over the periphery of the base. In the preferred form, though not necessary to the invention, a cutout portion 23 is formed in the lip 22 to enable the user to grasp the base to remove the cover from the base. The cover may be made of a sterilizable material.

The base may be transparent or opaque. The cover is preferably transparent, or includes a transparent top. The materials of which these structures are made is not critical, it is important only that they provide adequate structural rigidity and permit the system to perform the functions as described. Typically, these structures are made of one of many polymers, polycarbonates and some vinyl copolymers, for example. Other polymers may, of course, be used very conveniently.

Figure 4:
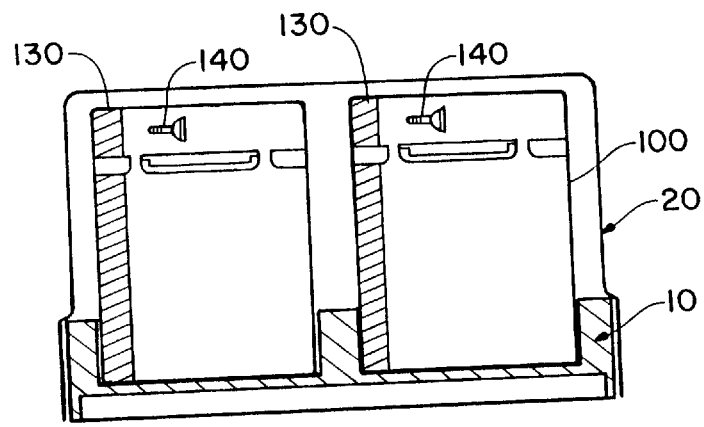
FIG. 4 is a cross-sectional view of the package depicted in FIG. 1 taken transversely along lines 4—4 of FIG. 1 showing the individual component packages, each of which is color coded, in display position in the display package depicted in FIG. 1.
Figure 5:
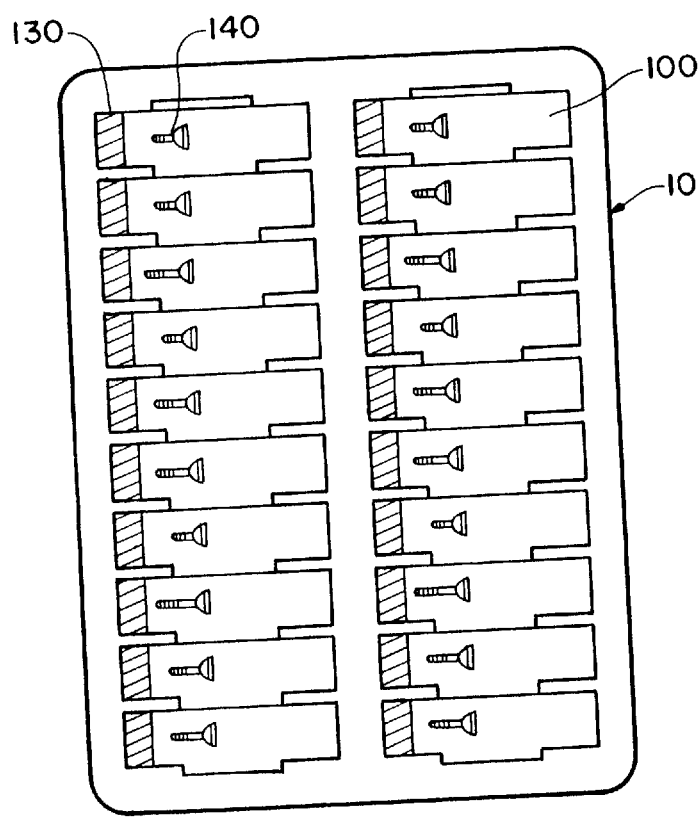
FIG. 5 is a top view, with the package cover removed, looking down upon the base of the display package holding a plurality of component packages showing the tops thereof with color coding and identifying indicia to permit simple and certain selection of a specific size of prosthetic component by the user.

As depicted in FIGS. 2, 4 and 5, the display package displays a plurality of individual component packages in the form of stepped back individual component boxes 100.

Figure 6:
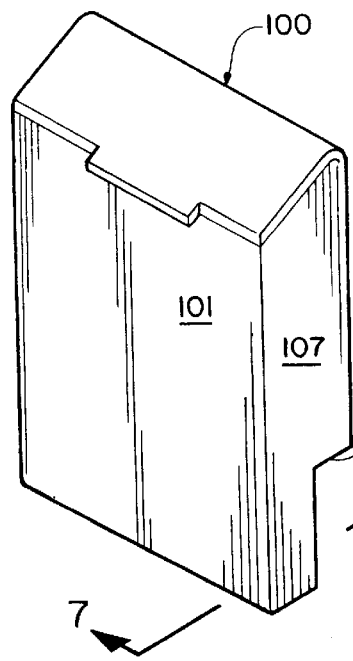
FIG. 6 is a perspective view of one of the component packages that are part of this invention, the label not being shown.
Figure 7:
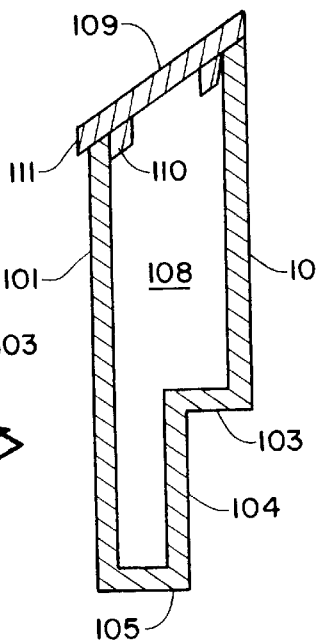
FIG. 7 is a vertical cross-sectional view of the package of FIG. 6 taken along lines 7—7 in the direction of the arrows.
Figure 8:
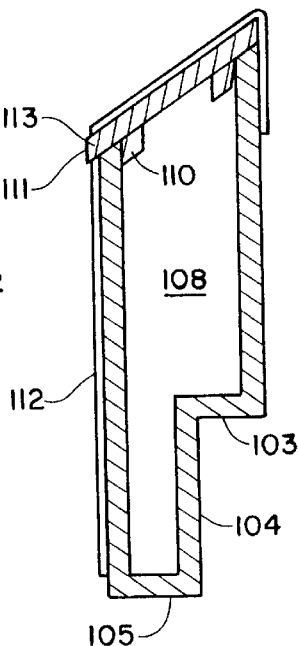
FIG. 8 is a vertical cross-sectional view of the package of FIG. 7, with a tamper indicator and identifying label adhesively bonded thereto.

FIG. 6 is a perspective view and FIG. 7 is a side elevation cross-sectional view of stepped back individual component box 100. As shown in FIGS. 6 through 9, the stepped back individual component box 100 comprises a full front panel 101, an upper back panel 102, a forwardly extended (toward the front panel) step 103, and a lower stepped panel 104 secured in box form by a bottom 105 and ends 107 and 108. A lid 109, which may include a downwardly extending flange 110, shown in FIGS. 7 and 8, and so that the lid snaps closed, is preferable provided with a tab 111 for grasping to open the top. A label 112, shown in FIGS. 8 and 9. Extends from the front panel 101 over the lid 109 and to upper back panel 102. A hinge for lid 109 is preferably formed by the label, however, a separate hinge may be provided or the hinge may be formed in a unitary box and hinge construction. The label 112 comprises an opening defined therein to accommodate the tab that extends forwardly from the front and two tear strips 113 and 114 which must be torn to open the lid. These tear strips, thus, comprise tamper indicators so that the user can check the container to make certain it has not been tampered with be opening it to use the component inside.

The component boxes are configured and constructed to fit inside the enclosure in at least one symmetrical column front to back, two such symmetrical columns being shown in FIG. 5. As shown in FIGS. 1 and 5, the base comprises symmetrical dividers in the receptacle defining a plurality of individual box receptacles arranged in symmetrical columns for receiving and positioning a plurality of component boxes. The bottom of each stepped back box fits into an individual box receiving receptacle with the back wall extending over and upward from the divider thus disposing the boxes in a front-to-back symmetrical columnar configuration.

The stepped back individual component box is secured in the closed position by a tamper indicating adhesively bonded label 112 which extends at least over a large portion of the front panel 101, over at least a portion of the front edge of the lid and over at least a portion of the lid 109 and onto the back of the box so that the package cannot be opened without tearing the label. In a preferred embodiment, the two strip portions 113 and 114 of the label connect the front to the top of the box on each side of the tab so that upon being opened these strip portions are torn apart. It is, therefor, impossible to tamper with the contents of the stepped back individual component box without indicating such tampering. In the preferred form, the label covers substantially the entire front panel and the lid and extends downwardly to the upper back panel.

Figure 9:
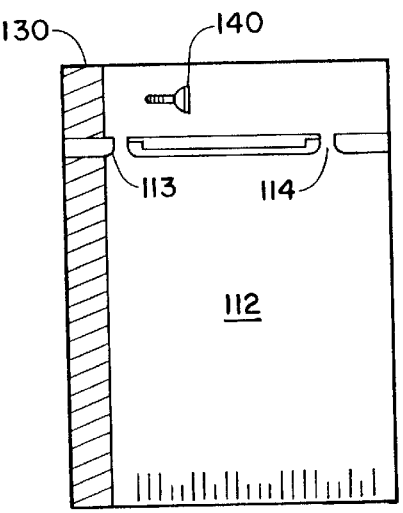
FIG. 9 is a front view of the component package of FIG. 6 showing the front face and the top, which is sloped downwardly toward the front, with a label upon which is printed identifying indicia to enable quick and certain size identification of the component in the package, the label comprising tamper indicator portions.

Indicia are printed on the label identifying the product, providing required information, dimensions, etc. as appropriate to the particular component contained in the stepped back individual component box. In particular, because the components are so small that individual sizes may appear to be the same and some components may appear to be the same to the unaided eye, specific indicia are printed on the label to be displayed on the front and/or top of the stepped back individual component box to identify both the product and the size. In practice, implants and dental prostheses are installed in sets of components scaled to a given diameter or length, etc. The individual components are also scaled and mate properly only with other components of the same set. Components of implants and dental prostheses having a diameter, for example, of 5 mm diameter may not be interchangeable with components for a 6 mm diameter implant. As shown in FIGS. 5 and 9, a colored strip 130 is provided on the label so as to be visible on the front and on the top, thereby indicating the size of the prosthesis with which the component is used. For example, a red stripe may indicate that the component is part of a 5 mm diameter set, a blue strip may indicate that the component is part of a 6 mm diameter set, etc.

In addition, a clear visual depiction of the component packaged in the stepped back individual component box is printed on the label, as indicated at 140 in FIGS. 5 and 9, to be visible on the top at least and desirably on the front of the stepped back individual component box.

The stepped back individual component box is desirably made of a transparent plastic, e.g., a polycarbonate of polymer or copolymer of styrene and/or vinyl chloride, however, the material is not critical and any material that is sufficiently strong and light may be used. It may be desirable to use a polymer which is sufficiently flexible in thin sections to form the hinge line.

Figures 10, 11:
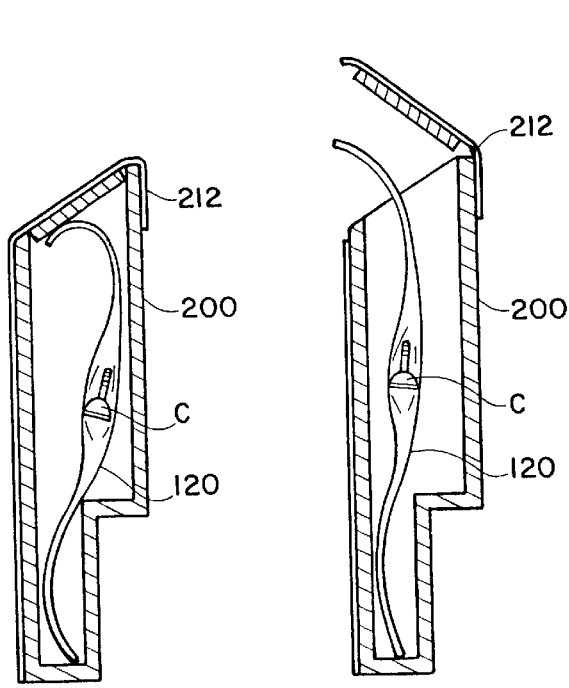
FIG. 10 is a side view, in partial cross-section of component package which is simplified as an alternative embodiment and for clearer illustration, showing the component package with a resiliently flexible envelope package enclosing a sterile dental prosthesis component in the package, the package being closed.
FIG. 11 is a side view of the package depicted in FIG. 10 with the top lid of the component package open and the edge of the resiliently flexible envelope extending upwardly to enable the user to grasp the same and remove it from the individual component package.

In one advantageous aspect, the individual component C, as shown in FIGS. 10 and 11, is sealed in an envelope 120 or other package formed of a sterilizable at least partially transparent resilient polymer. A simplified alternative embodiment of the stepped box, shown at 200, is shown in these figures for clarity of illustration and as an alternative which is less expensive to manufacture. The box 200 is essentially the same as the box 100 except that the flange on the top is omitted. An adhesive label 212 comparable to label 112 is also used. It will be seen in FIG. 10 that the envelope can be bent sufficiently to place it entirely in the stepped back individual component box. As shown in FIG. 11, once the lid of the stepped back individual component box is opened the envelope springs upwardly to extend from the box so as to permit the user to conveniently grasp the envelope and remove it from the box without damaging the envelope, thereby risking contamination. The envelope can then be opened by tearing or using sterile scissors, etc. and the component removed using a sterile tool or holder. The container and display system of this invention thus, in its preferred embodiment, comprises a resiliently flexible envelope in each of the component boxes and a dental prosthesis or a component of a dental prosthesis inside the resiliently flexible envelope. The resiliently flexible envelope is so configured and constructed that when it is contained in the component box it is under bending stress and when the top of the component box is opened such stress is relieved by extension of the envelope through the open top of the individual component container.

The envelope may comprise any transparent polymer which is flexibly resilient enough to be folded and yet to retain sufficient resilience to return to an extended position when the box is opened. The material should also be capable of being sterilized. Sterilization can be accomplished by heat or radiation, or in any manner which is reliable. Materials such as Mylar® polyethyleneterphthalate, nylon, etc. may be used. Certain cellulose ester films as well as parchment paper may also be used to form the envelope. In a highly preferred embodiment, one side of the envelope is formed of a polymer that becomes opaque upon radiation sterilization. This feature permits the manufacturer to visually determine whether or not the package has been sterilized before it is shipped and permits the dentist or surgeon to determine visually whether the package was sterilized. This double check system provides greater assurance that no non-sterile product will be used. Materials suitable for forming the package are commercially available. One such material being GEON RX® medical grade vinyl polymers available from B. F. Goodrich Company. Geon RX medical grade polymers are rigid and flexible vinyl products which are gamma-ray sterilisable. Other such materials are also available commercially.

It will be apparent from a review of the foregoing that a convenient display and packaging system is provided which provides for compact storage, convenient display, and ready and safe access has been provided.

Industrial Application

This invention is useful in dentistry and in the dental prosthesis industry.

What is claimed is:

1. A dental prosthesis component container and display system for containing sterile dental implants and prostheses and components thereof for convenient use by a dentist or oral surgeon comprising, in combination:

a display package comprising a base and a transparent cover, the base comprising a peripheral frame defining a shallow receptacle compartment, the cover being formed in substantial part of transparent material and being constructed and configured to fit snugly over and extend above the base, the combined base and cover defining an enclosure visible through the cover from outside the enclosure;

a plurality of component boxes constructed and configured to fit inside the enclosure in at least one symmetrical column, each of said boxes comprising a bottom, walls and an openable top defining a component containing space;

a component of a dental prosthesis inside the component box; and indicia on the component boxes encoding information defining the size of the component contained therein.

2. The system of claim 1 further comprising indicia on the component boxes depicting the component contained therein.

3. The system of claim 2 further comprising a resiliently flexible envelope in each of the component boxes, a dental prosthesis or a component of a dental prosthesis being inside the resiliently flexible envelope, the resiliently flexible envelope being so configured and constructed that when it is contained in the component box it is under bending stress and when the top of the component box is opened such stress is relieved by extension of the envelope through the open top.

4. A dental prosthesis component container and display system for containing sterile dental implants and prostheses and components thereof for convenient use by a dentist or oral surgeon comprising, in combination:

a display package comprising a base and a transparent cover, the base comprising a peripheral frame defining a shallow receptacle compartment, the cover being formed in substantial part of transparent material and being constructed and configured to fit snugly over and extend above the base, the combined base and cover defining an enclosure visible through the cover from outside the enclosure;

a plurality of component boxes constructed and configured to fit inside the enclosure in at least one symmetrical column, each of said boxes comprising a bottom, walls and an openable top defining a component containing space; and a resiliently flexible envelope in each of the component boxes and a dental prosthesis or a component of a dental prosthesis inside the resiliently flexible envelope, the resiliently flexible envelope being so configured and constructed that when it is contained in the component box it is under bending stress and when the top of the component box is opened such stress is relieved by extension of the envelope through the open top.

5. A dental prosthesis component container and display system for containing sterile dental implants and prostheses and components thereof for convenient use by a dentist or oral surgeon comprising, in combination:

a display package comprising a base and a transparent cover, the base comprising a peripheral frame defining a shallow receptacle compartment and symmetrical dividers in the receptacle defining a plurality of individual box receptacles arranged in symmetrical columns;

the cover being formed in substantial part of transparent material and being constructed and configured to fit snugly over and extend above the base, the combined base and cover defining an enclosure visible through the cover from outside the enclosure;

a plurality of component boxes constructed and configured to fit inside the enclosure in at least one symmetrical column, each of said boxes comprising a bottom, front wall, back wall and an openable top defining a component containing space, the back wall comprising an upper back wall portion, a step portion extending toward the front wall and a lower back wall portion and being so configured and constructed that the bottom and lower back wall of each component box fit into an individual box receiving receptacle with the step extending over the divider and the upper back wall portion extending upwardly over the divider, thus disposing the boxes in a front-to-back symmetrical columnar configuration; and a dental prosthesis or a component of a dental prosthesis inside the component box.

6. The system of claim 5 further comprising indicia on the component boxes encoding information defining the size of the component contained therein.

7. The system of claim 6 further comprising indicia on the component boxes depicting the component contained therein.

8. The system of claim 5 further comprising a resiliently flexible envelope in each of the component boxes, the dental prosthesis or a component of a dental prosthesis being inside the resiliently flexible envelope, the resiliently flexible envelope being so configured and constructed that when it is contained in the component box it is under bending stress and when the top of the component box is opened such stress is relieved by extension of the envelope through the open top.

9. The system of claim 8 further comprising indicia on the component boxes encoding information defining the size of the component contained therein.

10. The system of claim 9 further comprising indicia on the component boxes depicting the component contained therein.

11. The system of claim 8 further comprising indicia on the component boxes depicting the component contained therein.

12. A dental prosthesis component container system for containing sterile dental implants and prostheses and components thereof for convenient use by a dentist or oral surgeon comprising, in combination: an individual component container, an openable top for the container, and a resiliently flexible envelope in the container, the component being inside the resiliently flexible envelope, the resiliently flexible envelope being so configured and constructed that when it is contained in the component box with the top closed the envelope is under bending stress and when the top of the component box is opened such stress is relieved by extension of the envelope through the open top.

13. A dental prosthesis component container comprising an at least partially transparent box that comprises a front panel, a bottom, a top and a stepped back panel, the top having a front edge and a back edge, the stepped back panel comprising a top generally flat panel portion adjacent the top, a bottom generally flat panel portion adjacent the bottom, and an intermediate step joining the top flat panel portion and the bottom flat panel portion, the intermediate step extending generally perpendicularly to the top generally flat panel portion and the bottom generally flat panel portion, the stepped back panel being longer that the front panel, the ends defining an edge at each end of the box tapering downwardly from the back panel to the front panel.

14. The container of claim 13 further comprising a flexible sheet label adhesively bonded to the front panel, the top and the back panel, the label forming a hinge securing the top to the back panel.

15. The container of claim 14 further comprising a tab extending from the front edge of the top.

16. The container of claim 15 wherein the label defines an opening for the tab to project through and at lease one tear portion connecting the front panel and the top, the panels, top and label being so constructed that the top cannot be opened without tearing the tear portion as an indication that the container has been tampered with.

17. The container of claim 13 further comprising a label adhesively bonded to the front panel, top and back panel, and wherein the label defines an opening for the tab to project through and at lease one tear portion connecting the front panel and the top, the panels, top and label being so constructed that the top cannot be opened without tearing the tear portion as an indication that the container has been tampered with.

18. A dental prosthesis component container comprising an at least partially transparent box that comprises a front panel, a stepped back panel, a bottom and ends, and a top, the top having a front edge and a back edge, the stepped back panel being longer that the front panel, the ends defining an edge at each end of the box tapering downwardly from the back panel to the front panel, and a flexible sheet label adhesively bonded to the front panel, the top and the back panel, the label forming a hinge securing the top to the back panel.

19. The container of claim 18 further comprising a tab extending from the front edge of the top.

20. The container of claim 19 wherein the label defines an opening for the tab to project through and at lease one tear portion connecting the front panel and the top, the panels, top and label being so constructed that the top cannot be opened without tearing the tear portion as an indication that the container has been tampered with.

21. The container of claim 19 wherein the label is adhesively bonded to the front panel, top and back panel, and wherein the label defines an opening for the tab to project through and at lease one tear portion connecting the front panel and the top, the panels, top and label being so constructed that the top cannot be opened without tearing the tear portion as an indication that the container has been tampered with.

* * * * *